(12) United States Patent
Iga et al.

(10) Patent No.: US 7,389,009 B2
(45) Date of Patent: Jun. 17, 2008

(54) OPTICAL FIBER SENSOR AND MEASURING APPARATUS USING SAME

(75) Inventors: Mitsuhiro Iga, Tokyo (JP); Kazuhiro Watanabe, Tokyo (JP); Atsushi Seki, Tokyo (JP)

(73) Assignee: Tama- Tlo, Ltd., Tokyo (JP)

( * ) Notice: Subject to any disclaimer, the term of this patent is extended or adjusted under 35 U.S.C. 154(b) by 0 days.

(21) Appl. No.: 10/575,718

(22) PCT Filed: Oct. 15, 2004

(86) PCT No.: PCT/JP2004/015266

§ 371 (c)(1),
(2), (4) Date: Apr. 13, 2006

(87) PCT Pub. No.: WO2005/038440

PCT Pub. Date: Apr. 28, 2005

(65) Prior Publication Data

US 2007/0077000 A1    Apr. 5, 2007

(30) Foreign Application Priority Data

Oct. 16, 2003   (JP) .............................. 2003-356225

(51) Int. Cl.
*G02B 6/00* (2006.01)
(52) U.S. Cl. .......................... 385/12; 385/14; 385/34; 385/77; 385/96; 385/124
(58) Field of Classification Search .................. 385/12, 385/14, 37
See application file for complete search history.

(56) References Cited

U.S. PATENT DOCUMENTS 4,894,532 A * 1/1990 Peterson et al. ............ 250/226
5,361,383 A * 11/1994 Chang et al. ................. 385/27
5,381,229 A * 1/1995 Murphy et al. ............. 356/477
5,477,323 A * 12/1995 Andrews et al. ............ 356/477
6,020,207 A * 2/2000 Liu ............................. 436/164

(Continued)

FOREIGN PATENT DOCUMENTS

JP       2000-121552 A       4/2000

(Continued)

*Primary Examiner*—Brian Healy
*Assistant Examiner*—Hung Lam
(74) *Attorney, Agent, or Firm*—Birch, Stewart, Kolasch & Birch, LLP

(57) ABSTRACT

An optical fiber sensor enabling simpler detection of a state of an external environment and a measuring apparatus using the same are provided. At a front end of an optical fiber portion 20*a* for transmitting the light a hetero core having a different diameter from that of a core of the optical fiber portion 20*a* is melt bonded so as to form a tip type optical fiber sensor 9 having a sensor portion 4 comprised of the hetero core on its front end. An end of the optical fiber portion 20*a* side of this tip type optical fiber sensor 9 has a light source 1 connected to it. Returned light striking the optical fiber portion 20*a* from the light source 1 and subjected to interaction with a measurement medium MD at the sensor portion 4 is split by an optical fiber coupler 2 and received at a photodiode or spectrum analyzer 6, thereby an optical fiber sensor measuring apparatus 100 is constructed.

6 Claims, 10 Drawing Sheets

U.S. PATENT DOCUMENTS

| | | | |
|---|---|---|---|
| 6,449,400 B1 * | 9/2002 | Watanabe et al. | 385/12 |
| 2003/0133654 A1 * | 7/2003 | Chang | 385/34 |

FOREIGN PATENT DOCUMENTS

| | | |
|---|---|---|
| JP | 2001-337036 A | 12/2001 |
| JP | 2002-350335 * | 12/2002 |
| JP | 2002-350335 A | 12/2002 |

* cited by examiner

90 OPTICAL FIBER SENSOR

OPTICAL FIBER SENSOR AND MEASURING APPARATUS USING SAME

TECHNICAL FIELD

The present invention relates to a tip type optical fiber sensor for detecting the state of an external environment at a front end of an optical fiber and a measuring apparatus using the same.

BACKGROUND ART

Attempts at utilizing-an optical fiber for the purpose of for example sensing a liquid and detecting the concentration of that liquid have been known.

As one type of sensor utilizing an optical fiber, a "hetero core" type optical fiber sensor comprised of an optical fiber at the middle of which a portion of a different core diameter known as a "hetero core" is melt bonded is known. By providing this hetero core, it becomes easier to generate interaction between light used for the sensing and the outside of the sensor.

For example, Patent Document 1 discloses an example of a hetero core type optical fiber sensor.

In Patent Document 1, a hetero core is melt bonded to the front end of an optical fiber. Then, the optical fiber side end of this hetero core type optical fiber sensor at the front end of which the hetero core is bonded is connected to an OTDR (Optical Time-Domain Reflectometer).

By making light strike the hetero core type optical fiber sensor from the OTDR and measuring an intensity of backward scattered light generated in the hetero core by the OTDR, the presence of a liquid, the concentration of the liquid, or other aspects of the state of the external environment can be detected in accordance with the change in intensity of the backward scattered light.

Patent Document 1: Japanese Patent Publication (A) No. 2002-350335 (FIG. 4)

Non-patent Document 1: Kasai, "Bio-sensor utilizing Surface Plasmon Resonance (SPR)" *Protein Nucleic Acid Enzymes*, vol. 37, no. 15 (1992) pp. 2977-2984

DISCLOSURE OF THE INVENTION

Problem to be Solved by the Invention

However, Patent Document 1 discloses and suggests only that the sensing be carried out by utilizing the backward scattered light measured by using an OTDR. It is considered difficult to avoid for example the following inconvenience.

For example, an OTDR is a device used for measurement by amplifying very weak backward scattered light. For this reason, an OTDR is expensive. Therefore, when using an OTDR, reduction of cost of the overall sensor system becomes difficult. Further, since very weak backward scattered light is used, a certain degree of precision in setting is necessary, so it is difficult to say to sensing is easily possible. When using backward scattered light, it is also necessary to differentiate between the light due to Fresnel reflection and the backward scattered light, so it is difficult to directly and simply obtain sensing results.

An object of the present invention is to provide an optical fiber sensor enabling more simple detection of the state of the external environment.

Further, another object of the present invention is to provide a measuring apparatus able to more simply detect the state of the external environment and measure predetermined characteristics by using the above optical fiber sensor and which is also easily produced.

Means for Solving the Problems

An optical fiber sensor according to the present invention is an optical fiber sensor having an optical fiber portion for transmitting light and a mode restriction releasing means including a light permeable member melt bonded to a front end of the optical fiber portion, guiding at least a portion of the light transmitted by the optical fiber portion to the outside of a core to release the restriction of the mode of the light, and returning the light released in the restriction of the mode into the core.

Alternatively, the optical fiber sensor according to the present invention may be structured as an optical fiber sensor having an optical fiber portion for transmitting light and a hetero core provided with a light transmitting core having a different diameter from the core of the optical fiber portion and able to transmit light propagated through the core, guiding at least a portion of the light propagated through the core from a boundary between the core and the light transmitting core to the outside of the core, and shorter in comparison with the length of the optical fiber portion, wherein the hetero core is melt bonded to the front end of the optical fiber portion.

A measuring apparatus according to the present invention is a measuring apparatus comprising an optical fiber sensor having an optical fiber portion for transmitting light and a mode restriction releasing means including a light permeable member melt bonded to the front end of the optical fiber portion, guiding at least a portion of the light transmitted by the optical fiber portion to the outside of the core to release the restriction of the mode of the light, and returning the light released in the restriction of the mode to the core; a light source connected to an optical fiber portion side end of the optical fiber sensor and emitting light to the core of the optical fiber sensor; and a light detecting means for detecting direct intensity of returned light returning to the light source side via the core subjected to interaction with the outside of the mode restriction releasing means in the mode restriction releasing means.

Alternatively, the measuring apparatus according to the present invention be structured as a measuring apparatus having an optical fiber sensor having an optical fiber portion for transmitting light and a hetero core provided with a light transmitting core having a different diameter from the core of the optical fiber portion and able to transmit light propagated through the core, guiding at least a portion of the light propagated through the core from a boundary between the core and the light transmitting core to the outside of the core, and shorter in comparison with the length of the optical fiber portion, wherein the hetero core is melt bonded to the front end of the optical fiber portion; a light source connected to the optical fiber portion side end of the optical fiber sensor and emitting light to the core of the optical fiber sensor; and a light detecting means for detecting direct intensity of returned light returning to the light source side via the core subjected to interaction with the outside of the hetero core in the hetero core.

In the present invention, the light source and the measuring apparatus are connected to one end of the optical fiber portion. The optical fiber portion transmits the light incident from the light source. The other end of the optical fiber portion has melt bonded to it for example a hetero core or other mode restriction releasing means provided with a light transmitting core having a different diameter from that of the core of the optical fiber portion and able to transmit light propagated through this core and shorter compared with the length of the optical fiber portion. The hetero core mode restriction releasing means releases the restriction of the mode of the light in the core by guiding at least a portion of the light propagated through the core of the optical fiber portion to the outside of this core. The light subjected to the interaction with the outside in a state where the restriction of the mode is released is transmitted again in the optical fiber portion via the core and returns to the light source side. The measuring apparatus connected to the light source side of the optical fiber portion detects the direct intensity of this returned light.

Effect of the Invention

According to the present invention, it becomes possible to easily provide an optical fiber sensor and a measuring apparatus able to simply detect and measure the characteristics of the external environment being measured.

BRIEF DESCRIPTION OF THE DRAWINGS

FIG. 1 is a schematic view of the configuration of a measuring apparatus using a tip type optical fiber sensor according to a first embodiment of the present invention.

[FIG. 2]

FIG. 3 is a schematic enlarged sectional view of the sensor portion shown in FIG. 2A.

FIG. 4 is a graph showing a relationship between a wavelength of light and an intensity obtained when a concentration of glycerin is measured by using a tip type optical fiber sensor measuring apparatus according to the first embodiment.

FIG. 5 is a graph showing a relationship between a wavelength of light and an intensity when a conventional optical fiber sensor measuring apparatus is used.

FIG. 6 is an example of the schematic configuration of a conventional optical fiber sensor measuring apparatus.

FIG. 7 is a graph of relationships of refractive indexes and intensities of light obtained by the optical fiber sensor measuring apparatus according to the first embodiment and the conventional measuring apparatus.

FIG. 8 is a sectional view of a modification of the optical fiber sensor according to the first embodiment.

[FIG. 9]

[FIG. 10]

DESCRIPTION OF NOTATIONS

Figure 1:
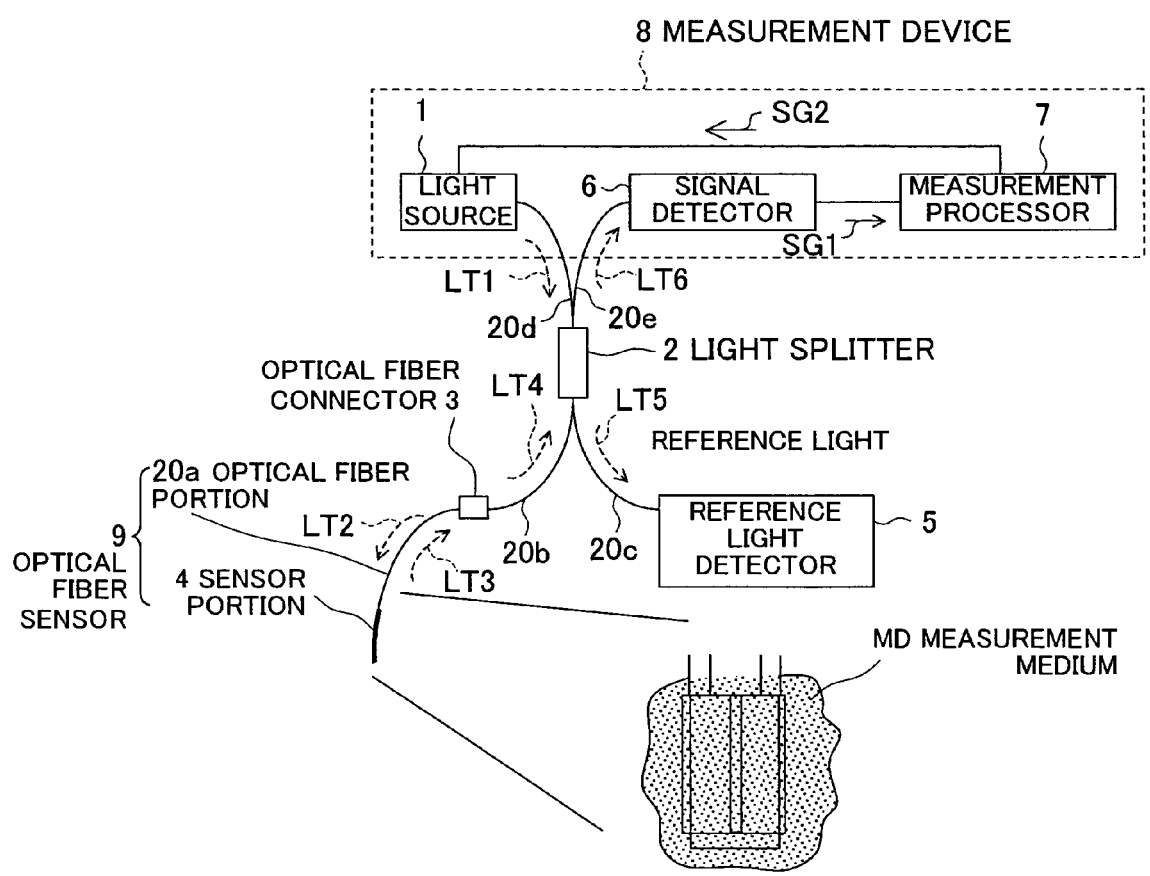
[FIG. 1]

1 . . . light source
2 . . . light splitter
3 . . . optical fiber connector
4 . . . sensor portion
5 . . . reference light detector
6 . . . signal detector (light detecting means)
7 . . . measurement processing (measuring means)
9 . . . tip type optical fiber sensor
20a to e . . . optical fiber portion
21, 31 . . . core
22, 32 . . . cladding
30 . . . hetero core
50 . . . metal film
60 . . . reflection film
100 . . . tip type optical fiber sensor measuring apparatus
500 . . . detection chemical immobilizing film

BEST MODE FOR WORKING THE INVENTION

Below, embodiments of the present invention will be explained with reference to the attached drawings.

First Embodiment

FIG. 1 is a schematic view of the configuration of a measuring apparatus using a tip type optical fiber sensor according to a first embodiment of the present invention.

A tip type optical fiber sensor measuring apparatus 100 shown in FIG. 1 has a light source 1, a light splitter 2, an optical fiber sensor 9, a reference light detector 5, a signal detector 6, and a measurement processor 7.

An embodiment of the light detecting means of the present invention corresponds to the signal detector 6. Further, an embodiment of the measuring means in the present invention corresponds to the measurement processor 7.

The light source 1 is connected to the light splitter 2 by an optical fiber portion 20d, while the signal detector 6 is connected to the light splitter 2 by an optical fiber portion 20e.

Further, the optical fiber sensor 9 is connected to an optical fiber portion 20b via an optical fiber connector 3. This optical fiber portion 20b is further connected to the light splitter 2.

The reference light detector 5 is connected to the light splitter 2 via an optical fiber portion 20c.

The optical fiber sensor 9 has a sensor portion 4 at one end of an optical fiber portion 20a. The other end of the optical fiber portion 20a is connected to the optical fiber portion 20b via the optical fiber connector 3.

The optical fiber portions 20a to 20e are constituted by using optical fibers. As optical fibers constituting the optical fiber portions 20a to 20e, use may be made of single mode optical fibers or multi-mode optical fibers. The types of optical fibers constituting the optical fiber portions 20a to 20e may be different from each other as well.

Further, lengths of the optical fiber portions 20a to 20e can be appropriately determined. For example, in a case of quantifying an object of measurement in a measurement sample in a laboratory, the lengths may be made several tens of centimeters. When it is necessary to separate the light source 1 and the sensor portion 4 in distance, for example the length of the optical fiber portion 20b or the optical fiber portion 20d may be made long. It is also possible to set the lengths of the optical fiber portions 20a to 20e to several hundreds of centimeters according to the mode of use.

The signal detector 6 and measurement processor 7 and the light source 1 and measurement processor 7 are connected by signal lines.

For example, as shown in FIG. 1, the light source 1, the signal detector 6, and the measurement processor 7 may be configured as one measurement device 8.

As the light source 1, either a multi-wavelength light source emitting light including light of a plurality of wavelengths or a single wavelength light source emitting monochrome light having any wavelength can be used. As a multi-wavelength light source, use is made of for example a white color light source, while as a single wavelength light source, use is made of for example a Llight emitting diode (LED) or laser diode (LD).

The light source 1 outputs light LT1 for measurement using the optical fiber sensor 9 to the light splitter 2.

The light splitter 2 is realized by for example an optical fiber coupler etc. which receives light at a single input port and splits and outputs the light to a plurality of output ports.

In the present embodiment, use is made of a 2×2 optical fiber coupler having two input ports and two output ports and fabricated by melt drawing. In this 2×2 optical fiber coupler, the light input to one input port is branched and output to two output ports.

Further, in this optical fiber coupler, if the input/output directions of the light are changed, the output ports function as the input ports, and the input ports function as the output ports.

As the optical fiber connector 3, use is made of for example a commercially available connector used for connecting optical fibers to each other. This optical fiber connector 3 is used for the connection of the optical fiber portion 20*a* of the optical fiber sensor 9 and the optical fiber portion 20*b*. When the optical fiber sensor is produced by directly providing the sensor portion 4 at the front end of the optical fiber portion 20*b*, this optical fiber connector 3 is unnecessary.

The optical fiber sensor 9 causes interaction of the light LT2 input via the light splitter 2, the optical fiber portion 20*b*, and the optical fiber portion 20*a* from the light source 1 with the external environment of the optical fiber sensor 9 in the sensor portion 4 and detects the state of the external environment.

Details of the configuration and functions of the optical fiber sensor 9 will be explained later.

The reference light detector 5 detects reference light LT5 branched from the light LT1 from the light source by the light splitter 2.

The reference light detector 5 is realized by for example a photodiode or a spectrum analyzer.

The reference light LT5 detected by the reference light detector 5 is used as a reference for canceling out instability such as time fluctuation of the light LT1 from the light source 1. For this reason, so far as the stability of the light source 1 is not considered in the precision of measurement, the reference light detector 5 is unnecessary. Further, the output port for splitting the light to the reference light detector 5 in the light splitter 2 is not necessary.

The signal detector 6 receives via the optical fiber portion 20*e* the returned light subjected to interaction with the external environment (outer world) outside of the optical fiber sensor 9 in the optical fiber sensor 9 and returning to the light source 1 side via the optical fiber portion 20*b* and the light splitter 2.

The signal detector 6 detects the intensity of the returned light. Namely, the signal detector 6 detects the direct intensity of the returned light from the optical fiber sensor 9.

The signal detector 6 transmits a data signal SG1 of the intensity of the detected light to the measurement processor 7.

As the signal detector 6, use is made of a light receiving circuit using for example a spectrum analyzer or photodiode. These detectors are suitably used in accordance with the type of the light source 1. For example, when white color light source is used as the light source 1, use is made of a spectrum analyzer for detecting the intensity of each of the light having wavelengths included in the light from the white color light source. When a single wavelength light source such as an LED or LD is used as the light source 1, a light receiving circuit using a photodiode is sufficient. A light receiving circuit using a photodiode is sometimes called a power-meter.

The measurement processor 7 is realized by a processing circuit such as a CPU (central processing unit) and a program for driving that.

The measurement processor 7 calculates the measurement value of the measurement object using the optical fiber sensor 9 based on the data signal SG1 transmitted from the signal detector 6. In other words, the measurement processor 7 converts information of the intensity of the light represented by the data signal SG1 to information of the presence of the measurement object in the external environment of the optical fiber sensor 9 and characteristics thereof such as concentration and degree of acidity by predetermined processing using this intensity. A program for conversion in accordance with the purpose of measurement is included in the measurement processor 7.

Further, for automation of the measurement, a configuration outputting a control signal SG2 from the measurement processor 7 to the light source 1 and making the measurement processor 7 control an on/off state of the light source 1 and the intensity, type, etc. of the light may be employed too.

Below, the optical fiber sensor 9 will be explained in detail.

Figure 2A:
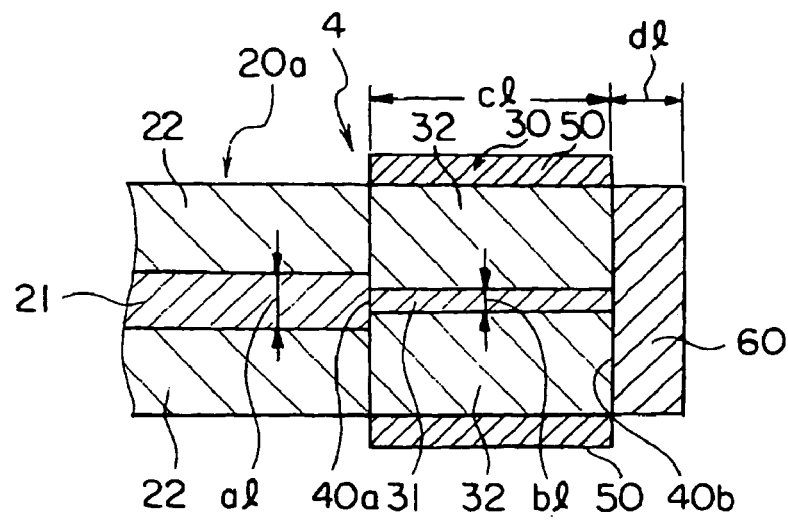
FIG. 2A to FIG. 2C are sectional views in a longitudinal direction in the vicinity of a sensor portion of an optical fiber sensor for showing the configuration of an optical fiber sensor according to the first embodiment.
Figure 2B:
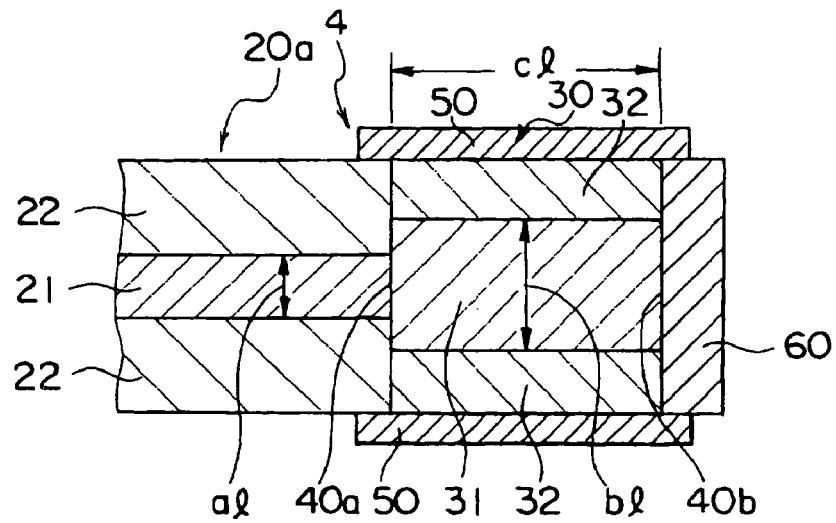
Figure 2C:
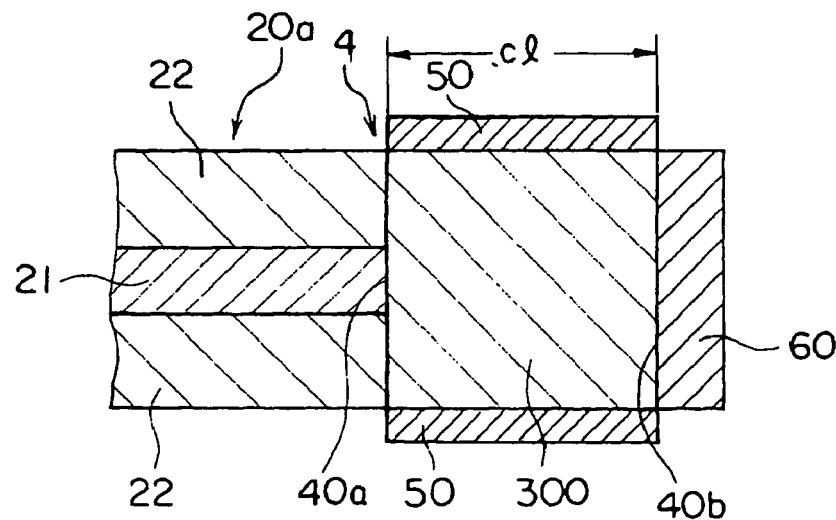

FIG. 2 is a sectional view in a longitudinal direction in the vicinity of the sensor portion 4 of the optical fiber sensor 9 for showing the configuration of the optical fiber sensor 9 according to the first embodiment. FIG. 2A to FIG. 2C show optical fiber sensors different in structures of sensor portions 4.

The optical fiber sensor 9 according to the present embodiment has the optical fiber portion 20*a* and the sensor portion 4.

The optical fiber portion 20*a* has a core 21 and a cladding 22 provided around that. The light from the light source 1 is made to strike the core 21.

Further, the sensor portion 4 according to the present embodiment has a hetero core 30, a metal film 50, and a reflection film 60.

An embodiment of the mode restriction releasing means in the present invention is the hetero core 30.

Further, an embodiment of the reflecting means in the present invention is the reflection film 60.

The optical fiber sensor 9 according to the present embodiment is configured by connecting a hetero core 30 of a few millimeters to a few centimeters length and shorter compared with the length of the optical fiber portion 20*a* to the end on an opposite side to the light source 1 side end of the optical fiber portion 20*a*. Accordingly, the optical fiber sensor 9 becomes a tip type optical fiber sensor having a hetero core 30 forming the sensor portion 4 at its front end.

FIG. 2A and FIG. 2B show hetero cores 30 each having a core 31, and a cladding 32 formed around that in the same way as the optical fiber portion 20*a*. A hetero core 30 having a diameter b1 of the core 31 smaller than a diameter a1 of the core 21 of the optical fiber portion 20*a* is shown in FIG. 2A, while a hetero core 30 having a diameter b1 larger than the diameter a1 is shown in FIG. 2B.

In this way, the diameter b1 of the core 31 is different from the diameter a1 of the core 21 of the optical fiber portion 20a, therefore the core 31 and the cladding 32 are called a "hetero core".

Note that the refractive index of the core 21 is slightly larger than the refractive index of the cladding arranged at the light source 1 side 22, and the refractive index of the core 31 is slightly larger than the refractive index of the cladding 32.

Both of the core 31 and cladding 32 are light permeable members and can transmit light therethrough.

In the hetero core 30 shown in FIG. 2A, the diameter b1 of the core 31 is made sufficiently smaller than the diameter a1 of the core 21. For example, a1=50 μm, and b1=3 μm.

In the hetero core 30 shown in FIG. 2B, the diameter b1 of the core 31 is made sufficiently larger than the diameter a1 of the core 21. For example, a1=50 μm, and b1=90 μm.

Further, the length c1 of the hetero core 3 is made for example 10 mm.

Further, as shown in FIG. 2C, for example, it is also possible to use a light permeable member 300 having a refractive index equivalent to that of the cladding 22 of the optical fiber portion 20a and able to transmit light in place of the hetero core 30. Such a light permeable member 300 can also be regarded as a type of hetero core having a core diameter b1 of 0.

The optical fiber portion 20a and the hetero core 30 or the light permeable member 300 are coaxially joined along the longitudinal direction at an interface 40a perpendicular to the longitudinal direction. When joining the hetero core 30 to the optical fiber portion 20a, the core 31 of the hetero core 30 and the core 21 of the optical fiber portion 20a are made to contact each other.

For the above joint, preferably use is made of the generally used melt bonding by electrodischarge.

As the optical fiber portion 20a and the hetero core 30, both of a single mode optical fiber and a multi-mode optical fiber can be used. They may be used in combination as well.

Below, for example, a case of joining a hetero core 30 using a single mode optical fiber (made by Newport Ltd., F-SA) having a core diameter b1 of about 3 μm to an optical fiber portion 20a using a multi-mode optical fiber (made by Osaki Electric Co., Ltd.) having a core diameter a1 of about 50 μm is explained as an example.

Due to the presence of the hetero core 30, at least a portion of the light propagated in the core 21 of the optical fiber portion 20a leaks to the outside of the core 21 at the interface 40a. At least a portion of the light guided and leaked to the outside of the core 21 is propagated in the cladding 32 of the hetero core 30. At this time, in the cladding 32 of the hetero core 30, the restriction of the mode of the light in the core 21 of the optical fiber portion 20a is released and broken.

In the hetero core 30, the releasing of the restriction of the mode of the light occurs irrespective of whether the type of the optical fiber used as the optical fiber portion 20a and the hetero core 30 is a single mode optical fiber or a multi-mode optical fiber.

Figure 3:
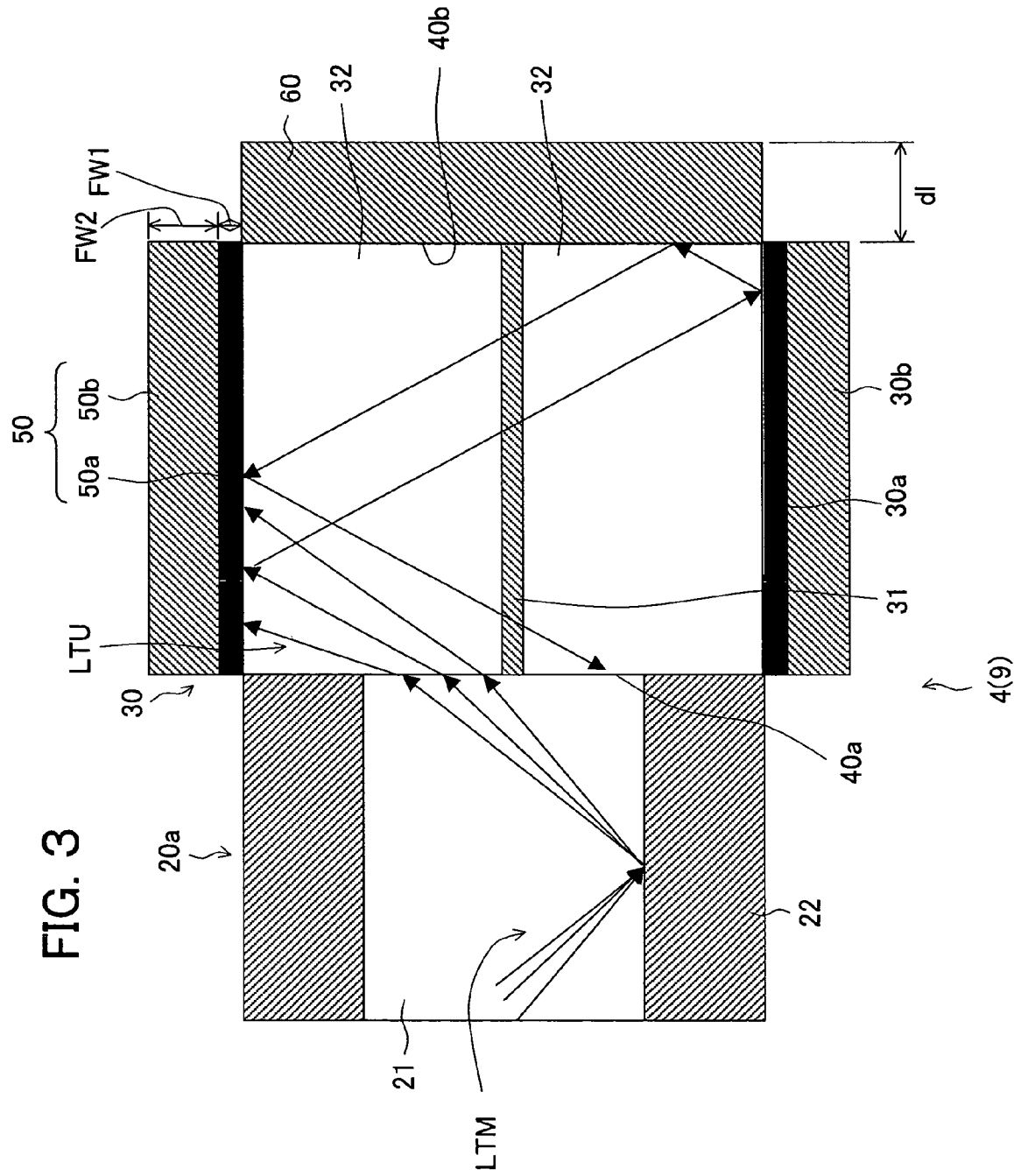
[FIG. 3]

FIG. 3 is a schematic sectional view showing enlarged a sensor portion 4 having a smaller core diameter b1 than the core diameter a1 as shown in FIG. 2A. Note., in FIG. 3, for clearer illustration, hatchings in the core 21 of the optical fiber portion 20a and the cladding 32 in the hetero core 30 are omitted.

A metal film 50 is coated by any method so as to cover the surface of the hetero core 30. In the present embodiment, for example a film 50a of chromium (Cr) is formed by vapor deposition on the outside surface of the hetero core 30, and a film 50b of gold (Au) is formed on this chromium film 50a by vapor deposition to thereby form the metal film 50.

A film thickness FW1 of the chromium film 50a is for example about several nm. A film thickness FW2 of the gold film 50b is for example about several tens of nm.

In detail, as will be explained later, by the reflection of the light inside the hetero core 30 at the boundary between the hetero core 30 and the metal film 50, surface plasmon is generated.

For example, the metal film 50 may be formed by using silver (Ag), aluminum (Al) or other metals as well.

In the first embodiment, in the hetero core 30, the surface of the end opposite to the end melt bonded to the optical fiber portion 20a is further provided with a reflection film 60.

The reflection film 60 is formed by for example the vapor deposition of silver.

The film thickness d1 of the reflection film 60 is set to an extent that the light in the hetero core 30 can be sufficiently reflected to the optical fiber portion 20a side. For example, the film thickness d1 is about several hundreds of nm.

If the light in the hetero core 30 can be sufficiently reflected to the optical fiber portion 20a side, the reflection film 60 may be formed by using a substance other than a metal such as silver.

By the front end of the hetero core 30 exhibiting a mirror surface state by the reflection film 60, the light in the hetero core 30 becomes easy to be reflected at the front end, and a larger amount of light begins to return to the optical fiber portion 20a side.

Here, the measurement using the measuring apparatus 100 according to the present embodiment will be explained. The optical fiber sensor 9 having the metal film 50 for generating the surface plasmon can be utilized for measurement of physical and chemical properties. The case where the concentration of the glycerin is measured will be explained as an example in the following description.

The sensor portion 4 according to the present embodiment is dipped in for example a solution containing the measured object, for example, glycerin, or other measurement medium MD so as to cover the surface of the hetero core 30 as shown in FIG. 1.

In this state, the light for measurement is emitted from the light source 1.

As shown in FIG. 1, the light LT1 emitted from the light source 1 strikes the light splitter 2 via the optical fiber portion 20d.

The light LT1 is split to two beams by the light splitter 2. One light LT2 reaches the sensor portion 4 via the optical fiber portion 20b and the optical fiber portion 20a of the optical fiber sensor 9. The other light LT5 strikes the reference light detector 5 via the optical fiber portion 20c as reference light.

In the core 21 of the optical fiber portion 20a, the light LT2 is propagated as light forming a plurality of modes due to the ordinary nature of an optical fiber. It is also possible to obtain a general grasp of the modes of the light transmitted by the optical fiber portion 20a as reflection angles of the light at the boundary between the core 21 and the cladding 22. When obtaining a grasp of the modes of the light as reflection angles, the reflection angles of the light in the optical fiber portion 20a can be considered as very many discrete angles. In FIG. 3, the light forming these plurality of modes is represented as a light LTM.

Note that, in the present embodiment, the measurement is carried out by utilizing the change of intensity of the light striking the optical fiber portion 20a from the light source 1, therefore it is sufficient to consider just the total light intensity of the group of modes with respect to one wavelength.

The diverse mode light LTM is released in restriction of the mode and broken in mode when it passes through the interface 40a and strikes the cladding 32 of the hetero core 30. In other words, in the hetero core 30, as shown in FIG. 3, the light begins to be propagated with a variety of reflection angles at the boundary between the cladding 32 and the metal film 50. This can be considered to be caused by the fact that various conditions determining the mode type (core diameter, refractive index, refractive index distribution) change when the light LTM strikes the hetero core 30 and the act that the fiber length, which is one factor of mode formation, is insufficient compared with the length of the hetero core 30. Accordingly, when the light LTM restricted to a certain mode strikes the hetero core 30, the restriction of that mode is released and the mode is broken, so the light becomes the light LTU reflected with a variety of reflection angles as shown in FIG. 3 and broken in mode and propagated in the cladding 32.

When the light is reflected at the boundary between the cladding 32 of the hetero core 30 and the metal film 50, interaction occurs between the light in the cladding 32 and the metal film 50, this affects the reflectance of the light, and therefore the reflectance changes. In most cases, the reflectance of the light is lowered and the intensity of the reflected light is reduced. This change of reflectance may occur also in a case where there is no metal film 50, but when the metal film 50 is provided, the change of the reflectance can be made larger due to the phenomenon called "surface plasmon resonance (SPR)", so the measurement of the change of intensity of the light can be facilitated. For the surface plasmon resonance phenomenon, refer to for example Non-patent Document 1 and other documents.

The reflectance of the light in the cladding 32 changes in accordance with the refractive index and light absorption ratio of the substance contacting the metal film 50 when the metal film 50 is provided. When the metal film 50 is not provided, the reflectance changes in accordance with the refractive index of the substance adhered to the outside surface of the cladding 32 and the light absorption ratio. Accordingly, by measuring the intensity of the light reflected at the hetero core 30, the characteristics such as the refractive index and light absorption ratio of a substance existing in the external environment of the sensor portion 4 can be determined. For example, the concentration of the glycerin in the measurement medium MD can be determined.

By the reflection of the light LTU broken in mode at the boundary between the metal film 50 and the cladding 32, it becomes possible to cause interaction between the light LTU and the external environment of the sensor portion 4 with a variety of reflection angles, that is, under many more conditions.

The light striking the cladding 32 of the hetero core 30 from the optical fiber portion 20a and becoming the light LTU broken in mode is propagated up to the front end of the hetero core 30 while being reflected at the boundary with the metal film 50. The reflection film 60 is provided on the interface 40b at the front end of the hetero core 30 so as to form a mirror surface, therefore the light LTU is reflected at the interface 40b and returns to the optical fiber portion 20a side while being reflected at the boundary with the metal film 50 again. In this way, by reflecting and returning the light LTU broken in mode at the front end of the sensor portion 4, the returned light returned to the optical fiber portion 20a side becomes light including a larger amount of information of the mutual interference in comparison with the light which only passed through the hetero core 30 in one direction.

The returned light LT3 returned into the core 21 of the optical fiber portion 20a again after the interaction with the external environment of the sensor portion 4 in the hetero core 30 reaches the light splitter 2 via the optical fiber portion 20b as the returned light LT4 shown in FIG. 1.

The returned light LT4 is split to two lights by the light splitter 2. One split light LT6 reaches the signal detector 6 via the optical fiber portion 20e.

The signal detector 6 detects the intensity of the light LT6. There is a correlation between the intensity of the light LT6 and the intensity of the light LT3, therefore, by detecting the change of intensity of the light LT6, the change of intensity of the returned light LT3 can be determined.

The measurement processor 7 measures the characteristics of the measurement object by using the previously acquired correlations between the known characteristics of the measurement object as explained above and the intensity of the light LT6 based on the information of the intensity of the light LT6 included in the data signal SG1 transmitted from the signal detector 6. For example, the measurement processor 7 calculates the concentration of the glycerin included in the measurement medium MD by the processing.

The above correlations are stored in a storage device such as a not shown memory as a LookUp Table. The measurement processor 7 suitably accesses this memory to acquire the correlations between the characteristics of the measurement object and the intensity of the light LT6.

Figure 4:
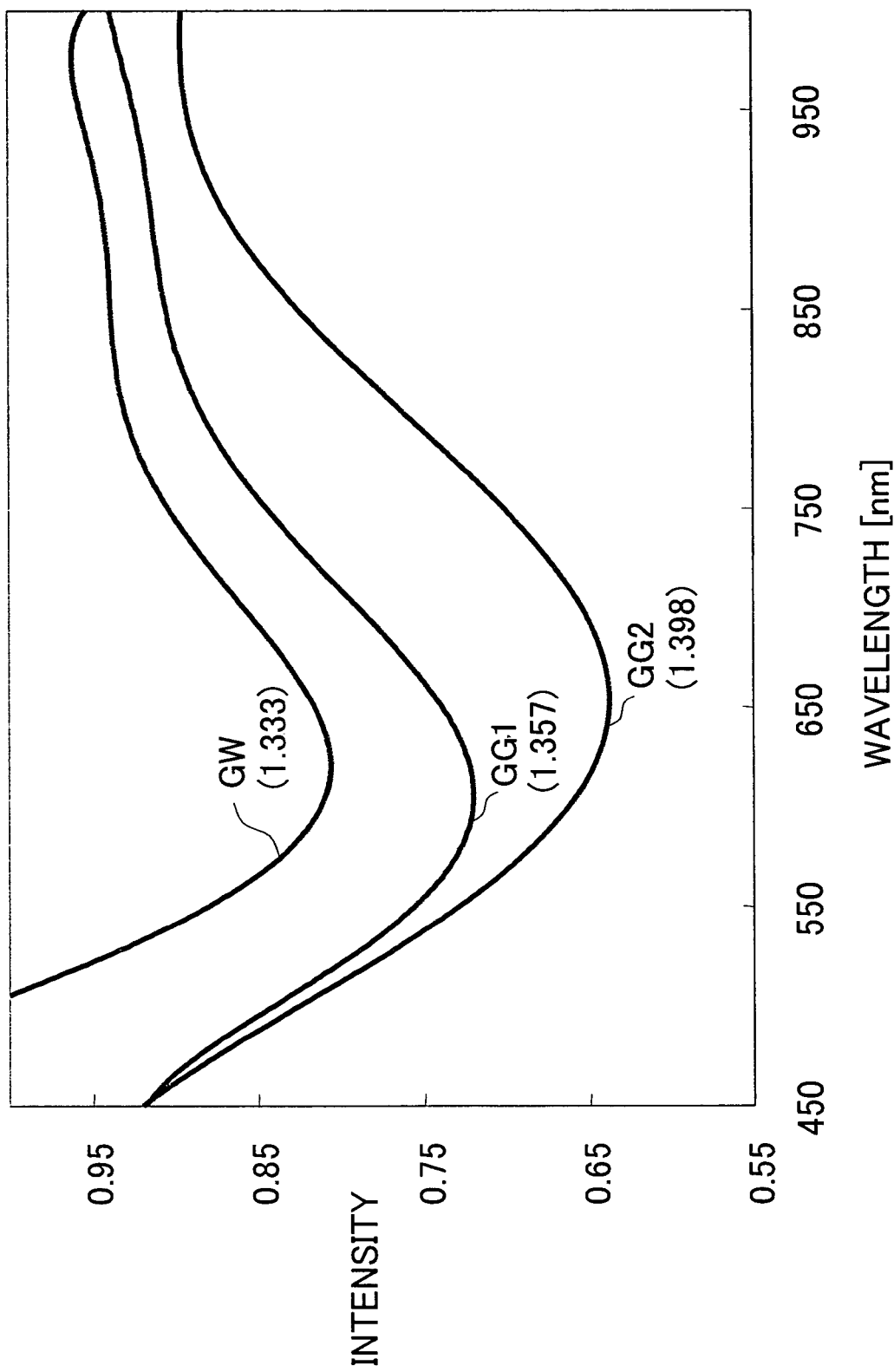
[FIG. 4]

FIG. 4 is a graph showing the relationship between the wavelength of the light LT6 and the intensity obtained in for example a case where the concentration of glycerin is measured by using the above tip type optical fiber sensor measuring apparatus 100. In FIG. 4, an abscissa represents the wavelength of the light LT6, and an ordinate represents the intensity of the light LT6 normalized using the light from the light source 1 as a reference. As the intensity of the light used as the reference, use may be made of the intensity of the reference light LT5 detected by the reference light detector 5 or use may be made of a set output light intensity of the light LT1 set with respect to the light source 1 by using a control signal SG2 from the measurement processor 7.

When performing the measurement shown in FIG. 4, the length cl of the hetero core 30 was set at 10 mm, the film thickness FW2 of the chromium film 50a was set at 4.4 nm, and the film thickness FW2 of the gold film 50b was set at 57.04 nm. Further, the film thickness dl of the reflection film 60 made of silver was set at 200 nm.

As shown in FIG. 4, in order to execute a sweep for checking the intensities at a variety of wavelengths, a white color light source was used as the light source 1. Spectrum analyzers were used as the reference light detector 5 and the signal detector 6 corresponding to the white color light source.

Water was used as the measurement medium MD. In the graph of FIG. 4, a curve GW shows the result of a case where the water content is 100%, a curve GG1 shows the result of a case where the glycerin concentration is 20%, and a curve GG2 shows the result of a case where the glycerin concentration is 50%.

Note that the refractive index of water is about 1.333, the refractive index of a glycerin 20% aqueous solution is about 1.357, and the refractive index of a glycerin 50% aqueous solution is about 1.398.

The curves shown in FIG. 4 are characterized in that the curves GW, GG1, and GG2 change relatively more gently in comparison with conventional cases and downward peaks are generated. Further, the curves GW, GG1, and GG2 are plotted so as not to cross each other within a range of wavelength broader than the conventional one.

Figure 5:
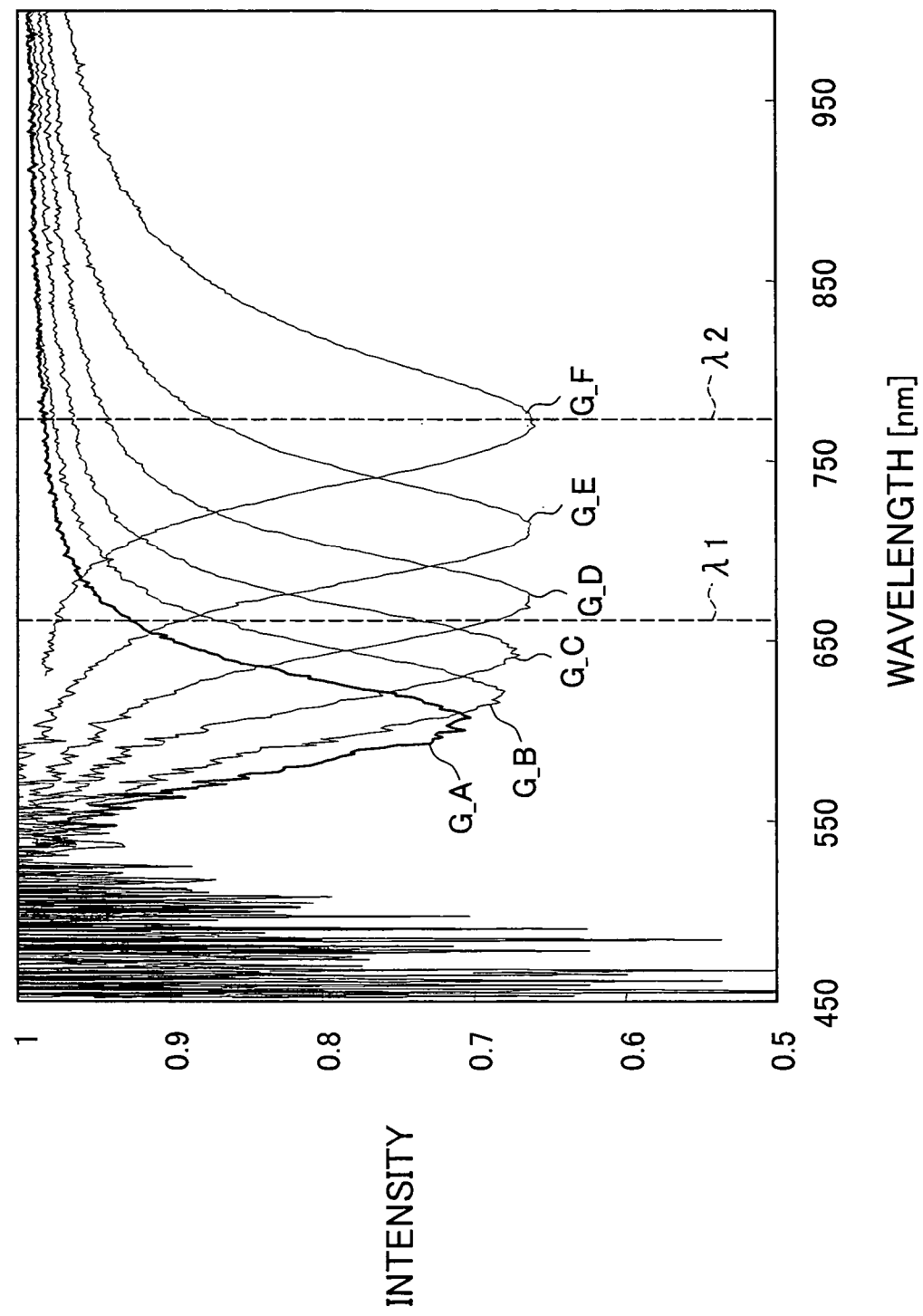
[FIG. 5]

For comparison, measurement results when using a conventional optical fiber sensor measuring apparatus are shown in FIG. 5.

In the graph shown in FIG. 5, the abscissa represents the wavelength, and the ordinate represents the normalized intensity of the light in the same way as FIG. 4.

Figure 6:
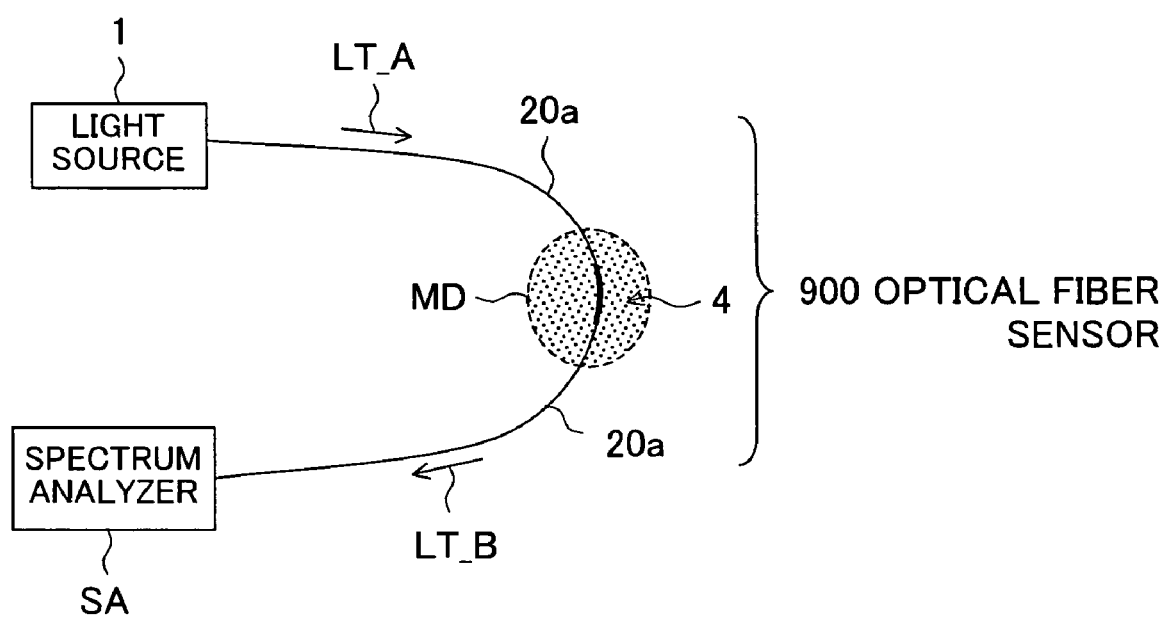
[FIG. 6]

Note that, FIG. 6 shows an example of a schematic configuration of a conventional optical fiber sensor measuring apparatus. The curves G_A, -, G_F shown in FIG. 5 are curves obtained as a result of measurement using an optical fiber sensor 900 having a structure providing the sensor portion 4 between two optical fiber portions 20a as shown in FIG. 6. In the two optical fiber portions 20a, ends opposite to ends on the sensor portion 4 side are connected to the light source 1 and the spectrum analyzer SA.

The sensor portion 4 shown in FIG. 6 exhibits the same structure as that of the sensor portion 4 according to the first embodiment shown in FIG. 3 except that the optical fiber portion 20a is connected in place of the reflection film 60. In the optical fiber sensor 900 shown in FIG. 6, the length cl of the hetero core 30 was set at 10 mm.

Note that in the optical fiber sensor 900, the film thickness FW1 of the chromium film 50a was set at about 5 nm, and the film thickness FW2 of the gold film 50b was set at about 60 nm.

The sensor portion 4 shown in FIG. 6 is made to contact the measurement medium MD. In this state, white color light LT_A emitted from the light source 1 is propagated through the optical fiber portion 20a, reaches the sensor portion 4, and interacts with the measurement medium MD in the external environment of the sensor portion 4 in the sensor portion 4. The light LT_B after the interaction in the sensor portion 4 is propagated through a latter stage of the sensor portion 4, that is, the optical fiber portion 20a existing on the emission side of the light, and reaches the spectrum analyzer SA.

The spectrum analyzer SA detects the intensity of the light LT_B.

The curves G_A, -, G_F of FIG. 5 show light intensities at different wavelengths of the light LT_B when the refractive index of the measurement medium MD in FIG. 6 is changed by changing for example the concentration of the measurement object.

The curves G_A, G_B, G_C, G_D, G_E, and G_F represent results of cases where the refractive indexes of the measurement medium MD are 1.333, 1.345, 1.357, 1.371, 1.384, and 1.398.

When comparing FIG. 4 and FIG. 5, in the case of FIG. 5 using the conventional optical fiber sensor 900, within the range of wavelength of 550 nm or more, it is seen that the curves change more sharply than the case of FIG. 4 and that downward peaks are formed. Further, it is seen that the curves G_A and G_F of FIG. 5 cross each other.

When the curves cross as in FIG. 5, the wavelengths useable for the measurement of the refractive index and the concentration and other characteristics which can be calculated from the refractive index are restricted, therefore the measurement becomes difficult. For example, in a wavelength $\lambda_1$ (about 656.8 nm) shown in FIG. 5, irrespective of the fact that the refractive index is larger in the case of the curve G_E than the case of the curve G_C, the intensity becomes smaller in the case of the curve G_E than the case of the curve G_C. In this way, it is difficult to use, for the measurement, light having a wavelength within a range where the trend of the change of the refractive index and the trend of the change of the intensity differ. For this reason, for example, it is necessary to use, for the measurement, light having a wavelength within a range where there is uniformity in the trend of the change of the refractive index and the trend of the change of the intensity like the wavelength $\lambda_2$ (about 769.6 nm)

However, in the case where the curves tend to sharply change as in FIG. 5, even in the case of the wavelength $\lambda_2$, the intervals between the curves tend to become narrower, for example, between the curves G_A, G_B, and G_C. For this reason, conventionally, it tended to be difficult to derive the change of characteristics such as the refractive index from the change of intensity.

On the other hand, in the case of the first embodiment as shown in FIG. 4, each curve gently changes and the intervals between one curve and another become broader than the conventional intervals, therefore, even when light of for example the wavelength $\lambda_2$ is used, the characteristics such as the refractive index can be easily measured.

The reason why the curves do not cross and gently change, that is, the characteristics of the measurement object begin to more clearly appear in each wavelength, in this way is considered to be that the hetero core 30 or other mode restriction releasing means is bonded to the front end of the optical fiber portion 20a, and the light is reflected at the portion of this hetero core 30 and returned to the optical fiber portion 20a side. That is, in the hetero core 30, light in a certain mode where the reflection angle is substantially constant does not interact with the external environment. Rather, the light LTU broken in mode and having a variety of reflection angles interacts with the external environment. Therefore, sharp peaks do not easily form in the curves of the wavelength and intensity. Further, by the interaction of the light LUT having a variety of reflection angles with the external environment, the detection of characteristics of the measurement object becomes easy, therefore the change of the characteristics of the measurement object easily appears as the change of intensity. As a result, the intervals between curves at the same wavelength become broader. Further, by the reflection of the light LTU broken in mode at the front end of the hetero core 30 and returning to the optical fiber portion 20a side, the interaction between the light LTU and the external environment is simply repeated about double the number of times, therefore the trend of the intervals between curves becoming broader and the peaks becoming gentler described above becomes stronger.

Figure 7:
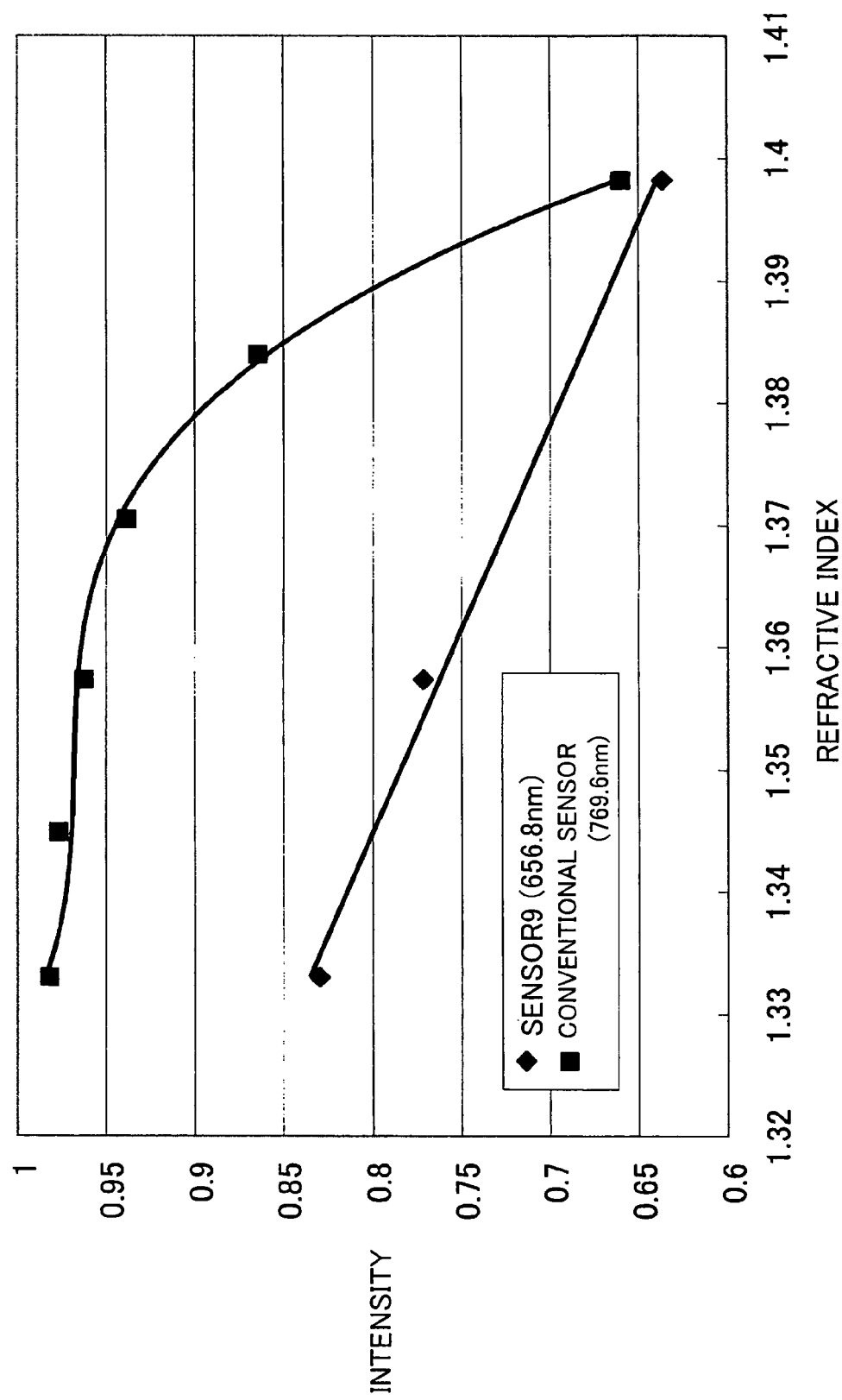
[FIG. 7]

A graph rearranging the above results from the viewpoint of the refractive index is the graph shown in FIG. 7. In the graph of FIG. 7, the abscissa represents the refractive index of the measurement medium MD, and the ordinate represents the intensity of the light detected by the signal detector 6 or the spectrum analyzer SA.

In FIG. 7, a plot indicated by the marks ♦ shows the result in the case where the relationship between the refractive index at a wavelength of 656.8 nm, that is, the wavelength $\lambda_1$ shown in FIG. 5, and the intensity of the light is measured by using the tip type optical fiber sensor measuring apparatus 100 according to the first embodiment. On the other hand, a plot indicated by the marks ■ shows the result in the case where the relationship between the refractive index at a wavelength of 769.6 nm, that is, the wavelength $\lambda_2$, and the intensity of the light is measured by using the conventional optical fiber sensor 900 shown in FIG. 6.

As shown in FIG. 7, in the case of the first embodiment, it is seen that the intensity and the refractive index have almost a linear relationship even in the case of the wavelength $\lambda_1$ where the measurement was conventionally difficult and that the measurement can be easily executed.

On the other hand, in the conventional case, even at the wavelength $\lambda_2$ where uniformity exists in the trend of the change of intensity and the trend of change of the refractive index, the linearity is poor between the intensity and the refractive index.

The optical fiber sensor 9 according to the present embodiment in which there is linearity between the intensity and the refractive index is more preferred as a sensor.

As described above, in the first embodiment, the front end of the optical fiber portion 20a has attached to it a mode restriction releasing means for releasing the restriction of the mode of the light LTM propagated in the core 21 and restricted in mode and forming the light LTU broken in mode. Inside the mode restriction releasing means, the light LTU broken in mode interacts with the external environment. Then, the light LTU interacting with the external environment and broken in mode is reflected by the reflection film 60 on the front end of the mode restriction releasing means and further interacts with the external environment. From the above, it becomes possible to broaden the range of wavelength of the light which can be used to detect the characteristics of a measurement object in the external environment and to make the detection characteristics linear when performing the measurement using an optical fiber.

As the mode restriction releasing means, it is possible to use a hetero core 30 or other member utilizing commercially available optical fiber. Also, a cutting system for cutting the optical fiber to form the hetero core 30 is commercially available. The generally used electrodischarge melt bonding can be used for the joint between the hetero core 30 and the optical fiber portion 20a. A melt bonding system is also commercially available. For this reason, it is possible to easily produce the tip type optical fiber sensor 9 and the measuring apparatus 100.

Further, in the first embodiment, the hetero core 30 is not nipped by the optical fiber portion 20a as shown in FIG. 6, but a structure in which the hetero core 30 is joined to the front end of the optical fiber portion 20a, and the light after the interaction occurs is returned to the optical fiber portion 20a side is employed. For this reason, laying and routing the optical fiber over the entire measuring apparatus such as the measuring apparatus 100 can be greatly simplified.

In order to stably generate the SPR with a large intensity, characteristics such as the roughness of the surface of the optical fiber for forming the metal film 50 are important, but commercially available optical fiber can be utilized in the hetero core 30 forming the metal film 50 thereon, therefore evaluation of the characteristics of the surface is easy, and the characteristics are stable. Accordingly, according to the optical fiber sensor 9 according to the present embodiment, it is possible to reliably generate a desired SPR.

Further, it is possible to make the outside diameter of the hetero core 30 for causing the light in the core 21 of the optical fiber portion 20a to interact with the external environment the same as the outside diameter of the optical fiber portion 20a. Due to this, it becomes possible to improve the intensity of the sensor portion 4 and to commercially use the optical fiber sensor 9.

In the measuring apparatus 100 according to the first embodiment, by breaking down the mode of the light in the hetero core 30, it becomes easy to reflect changes in characteristics of the measurement object in the external environment in the change of intensity of the returned light LT6. Accordingly, by detecting the direct intensity of the returned light LT6, it becomes possible to detect the characteristics of the measurement object. As a result, as the signal detector 6, it becomes possible to apply a much cheaper device than an OTDR (Optical Time-Domain Reflectometer) like a photodiode, and it becomes possible to reduce the price of the measuring apparatus 100. Further, it also becomes possible to reduce the size of the measuring apparatus 100 by using the tip type optical fiber sensor 9, using for example an LED as the light source 1, and using a photodiode as the signal detector 6.

[Modification]

Figure 8:
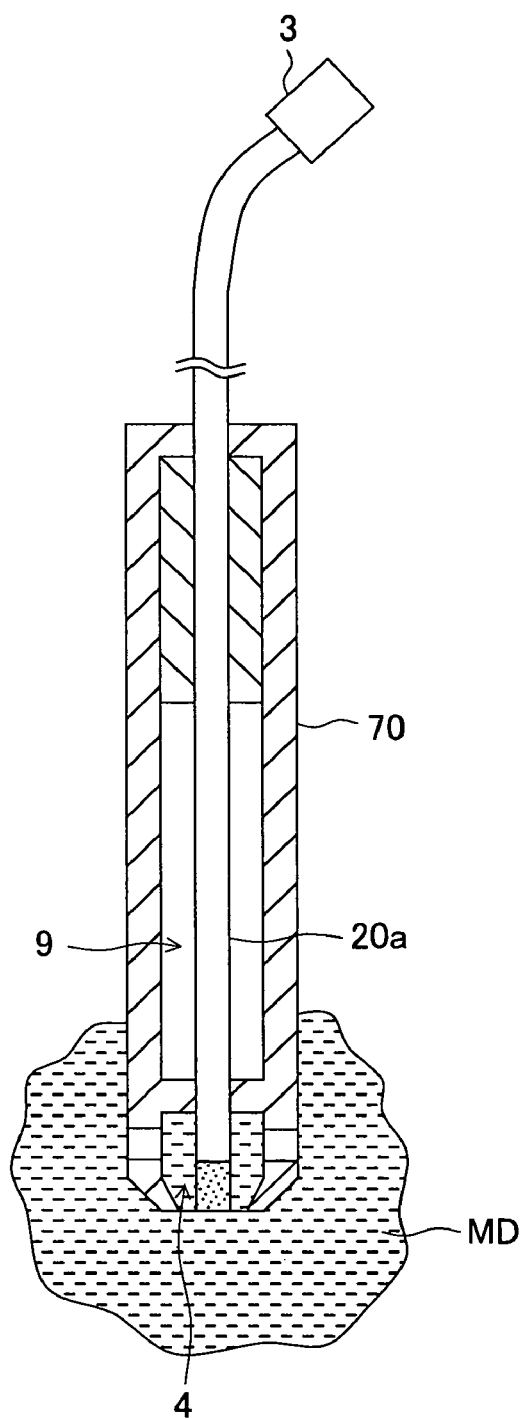
[FIG. 8]

FIG. 8 is a sectional view showing a modification of the optical fiber sensor 9 according to the first embodiment described above.

An optical fiber sensor 90 according to the modification shown in FIG. 8 is different from the optical fiber sensor 9 only in the point that the optical fiber sensor 9 according to the first embodiment is clamped and covered by a cover member 70. Accordingly, the same notations are attached to the same components, and detailed descriptions are omitted.

The cover member 70 is formed by a resin material such as a plastic.

The cover member 70 is given a shape running along the longitudinal direction of the optical fiber sensor 9, for example, a pen shape or stick shape.

The cover member 70 is fixed by clamping the optical fiber sensor 9. Only the front end including the sensor portion 4 in the optical fiber sensor 9 can contact the measurement medium MD.

The optical fiber sensor 90 as described above can be connected to the optical fiber portion 20b in FIG. 1 via the optical fiber connector 3 in the same way as the optical fiber sensor 9 and can be used for the measurement of a variety of characteristics such as the concentration of the measurement object.

According to the optical fiber sensor 90 having the cover member 70 as described above and the measuring apparatus using the same, in addition to the same effects as the case of the first embodiment, the effect that protection of the sensor portion 4 and handling become easier than with direct operation of the optical fiber sensor 9 can be obtained.

Second Embodiment

Figure 9A:
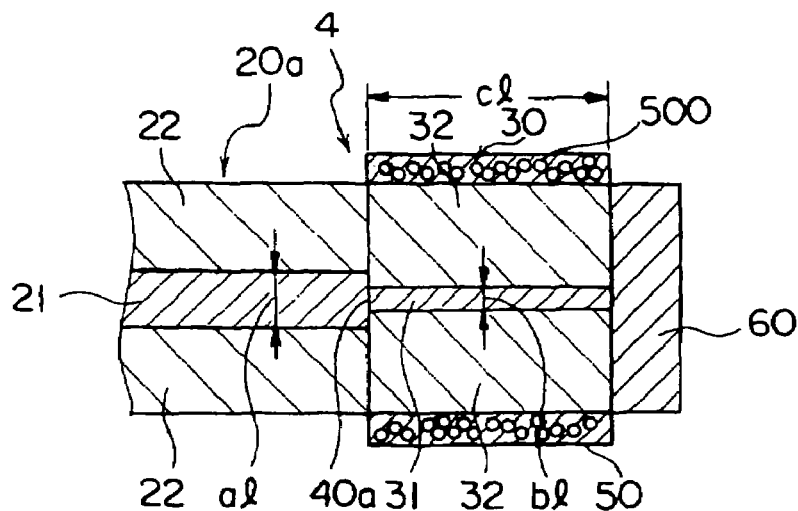
FIG. 9A to FIG. 9C are sectional views in the longitudinal direction in the vicinity of a sensor portion of an optical fiber sensor according to a second embodiment of the present invention.
Figure 9B:
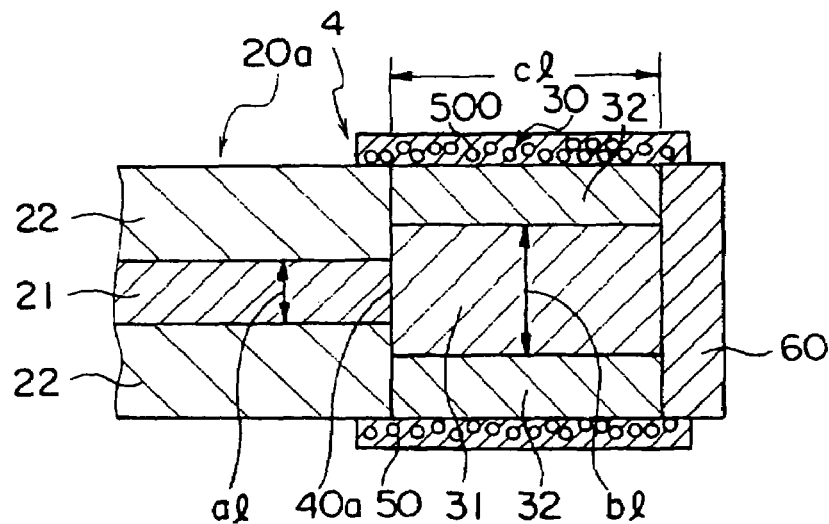
Figure 9C:
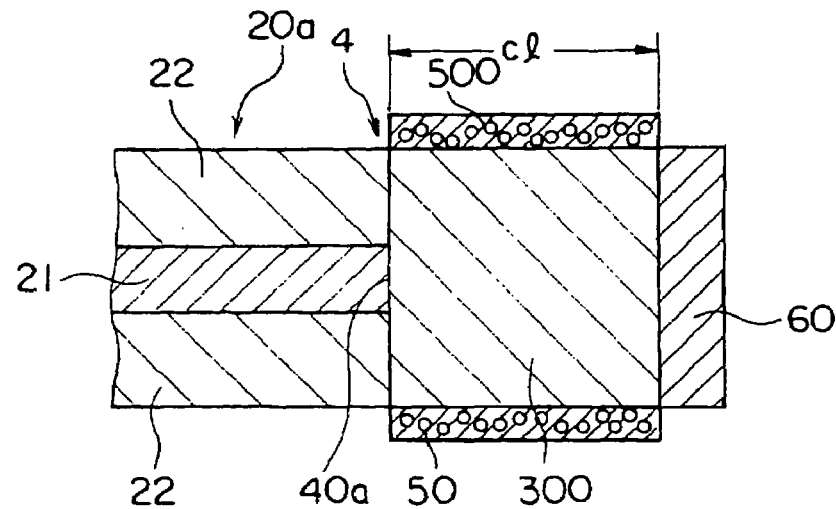

FIG. 9A to FIG. 9C are sectional views in the longitudinal direction in the vicinity of the sensor portion 4 of the optical fiber sensor according to a second embodiment of the present invention.

The optical fiber sensor according to the second embodiment and the measuring apparatus using the same are different from the case of the first embodiment only in the point that a detection chemical immobilizing film 500 is used in place of the metal film 50. Accordingly, the same notations are attached to the same components, and detailed descriptions are omitted.

FIG. 9A to FIG. 9C correspond to FIG. 2A to FIG. 2C and show different structures of the hetero core 30.

The detection chemical immobilizing film 500 is realized by a film formed by for example a sol gel process or a polymer film. For example, the detection chemical immobilizing film 500 is preferably formed as a porous film having very fine pores of a molecular level from the viewpoint that the detection chemical for immobilizing the detection chemical immobilizing film 500 and the measurement object can be more effectively reacted.

As the detection chemical, use can be made of a pH indicator detecting acidity or basicity or another functional dye or a metal indicator for detecting a specific metal or another chemical.

These detection chemicals can be immobilized to the detection chemical immobilizing film 500 by mixing them in when forming the detection chemical immobilizing film 500 by the sol gel process or can be chemically immobilized at the detection chemical immobilizing film 500 as well.

The detection chemical as explained above selectively reacts with the specific detection object in accordance with its type. By this reaction, the phenomenon that the light having a specific wavelength is absorbed or fluorescence occurs is generated in accordance with the characteristics (property of for example acid or base) of the detection object.

In response to the absorption of the light or fluorescence or other phenomenon, a change of spectrum, change of intensity, or other change is caused in the light LTU broken in mode inside the hetero core 30.

Accordingly, by detecting a change of spectrum or change of intensity of the returned light LT6 of the light LTU interacted with based on the reaction between the detection chemical and the detection object at the signal detector 6, it becomes possible to determine the presence of the detection object, that is, the measurement object, and characteristics such as the pH and the type.

As described above, according to the second embodiment, a detection chemical reacting with a specific measurement object is immobilized at the hetero core 30 by the detection chemical immobilizing film 500. Accordingly, in accordance with the type of the detection chemical, it becomes possible to selectively measure the measurement object, and further highly sensitive and highly precise measurement more than the case of the first embodiment can be carried out.

The detection chemical is immobilized at the sensor portion 4 side, therefore is not limited to a liquid as in the detection of for example ammonia. Detection and quantification of a measurement object included in a gas are also possible.

As described above, by changing the type of the detection chemical, it becomes possible to realize various types of sensors such as refractive index sensors, concentration sensors, and pH measurement sensors.

Third Embodiment

Figure 10A:
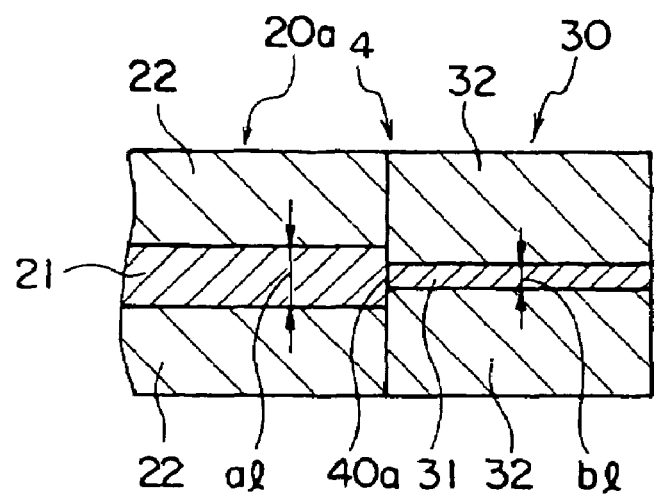
FIG. 10A to FIG. 10C are sectional views in the longitudinal direction in the vicinity of a sensor portion of an optical fiber sensor according to a third embodiment of the present invention.
Figure 10B:
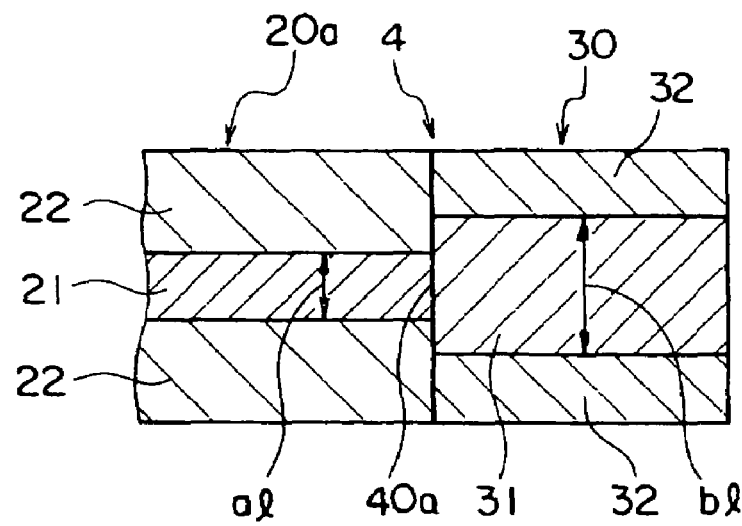
Figure 10C:
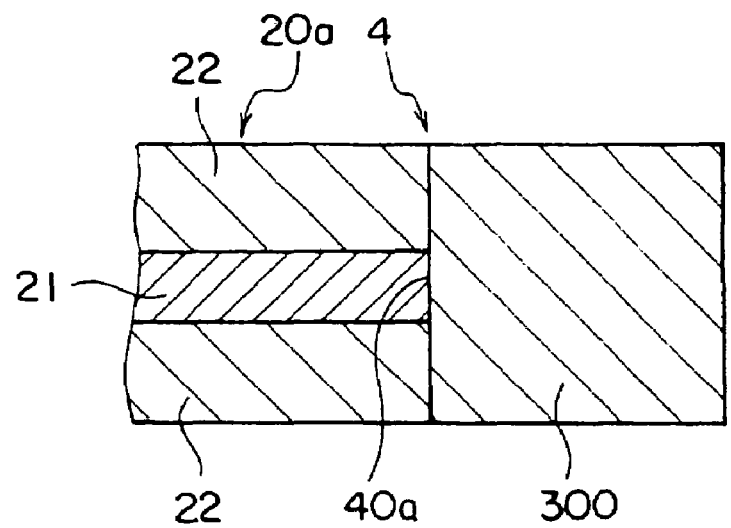

FIG. 10A to FIG. 10C are sectional views in the longitudinal direction in the vicinity of the sensor portion 4 of the optical fiber sensor according to a third embodiment of the present invention.

The optical fiber sensor according to the third embodiment and the measuring apparatus using the same are different from the cases of the first and second embodiments in the point that the metal film 50 or the detection chemical immobilizing film 500 is not provided, but the hetero core 30 is used as it is as the sensor portion 4. The rest of the points are substantially the same as the cases of the first and second embodiments, therefore the same notations are attached to the same components, and detailed descriptions are omitted.

FIG. 10A to FIG. 10C correspond to FIG. 2A to FIG. 2C or FIG. 9A to FIG. 9C and show different structures of the hetero core 30.

In the optical fiber sensor according to the third embodiment and the measuring apparatus using the same, the reflection film 60 is not provided on the front end of the hetero core 30. Even in the case where the reflection film 60 does not exist, due to the refractive index difference between the hetero core 30 and the external environment on the outside thereof, the light in the hetero core 30 is reflected to the optical fiber portion 20a side to a certain extent and returns.

In the optical fiber type sensor, in order to detect the characteristics of the state of the external environment of the sensor, it is sufficient so far as the light in the optical fiber can be made to interact with the outside. When sensitivity and selectivity are not needed, the metal film 50 and the detection chemical immobilizing film 500 are not necessary. Accordingly, as shown in FIG. 10A to FIG. 10C, even in the case where the sensor portion 4 is realized by using only the hetero core 30, detection of characteristics of the state of the external environment is possible.

Even in an optical fiber sensor melt bonding only the hetero core 30 to the optical fiber portion 20a, by the breakdown of the mode of the light in the hetero core 30, it becomes possible to make the detection characteristics linear.

Further, the characteristics of an optical fiber sensor of not requiring electric power at the part directly contacting the measurement object, so resulting in excellent prevention of explosions due to electric sparks and prevention of electric fires, of enabling remote monitoring due to the transmission of information by light, of enabling smaller size and lighter weight of the sensor portion 4, of enabling the optical fiber to be formed in variety of shapes since the optical fiber is flexible, and so on can be held as they are.

Note that the present invention is not limited to the above embodiments and the modification thereof. For example, in the second and third embodiments, a cover member like in the modification of the first embodiment may be provided as well. Further, the metal film 50 or the detection chemical immobilizing film 500 of the first and second embodiments may be provided on the surface of the hetero core 30 according to the third embodiment as well.

For example, the invention is not limited to dipping the sensor portion 4 in the measurement medium MD as in the embodiments. When leakage of the measurement object from a pipe etc. must be detected, the sensor portion 4 may be disposed at the desired measurement position of the piping as well.

INDUSTRIAL APPLICABILITY

The present invention can be used as a chemical sensor for example for measuring refractive index, sensing whether or not a liquid is present, measuring liquid concentration, sensing gas, measuring the gas concentration, measuring the concentration of protein, measuring the concentration of acid, measuring the degree of alkalinity, and sensing and measuring other chemical substances in accordance with the type of the metal film 50 or the type of the detection chemical immobilized at the detection chemical immobilizing film 500.

The invention claimed is:

1. An optical fiber sensor comprising:
   an optical fiber portion for transmitting light;
   mode restriction releasing means including a light permeable member melt bonded to a front end of the optical fiber portion, guiding at least a portion of the light transmitted by the optical fiber portion to the outside of a core to release a restriction of the mode of the light, and returning the light released in the restriction of the mode into the core, said mode restriction releasing means being a hetero core provided with a light transmitting core having a different diameter from the core of the optical fiber portion and able to transmit light propagated through the core and shorter in comparison with the length of the optical fiber portion; and further comprising:

a metal film provided at a surface side of said hetero core and generating surface plasmon by reflection of light in the hetero core at that surface; and reflection means for reflecting light in the hetero core and returning the light to said optical fiber portion side at the surface of the end of the hetero core opposite to the end melt bonded to the optical fiber portion.

2. An optical fiber sensor comprising:

an optical fiber portion for transmitting light;

mode restriction releasing means including a light permeable member melt bonded to a front end of the optical fiber portion, guiding at least a portion of the light transmitted by the optical fiber portion to the outside of a core to release a restriction of the mode of the light, and returning the light released in the restriction of the mode into the core, said mode restriction releasing means being a hetero core provided with a light transmitting core having a different diameter from the core of the optical fiber portion and able to transmit light propagated through the core and shorter in comparison with the length of the optical fiber portion;

a detection chemical immobilizing film selectively reacting with a detection object at the outside of said hetero core and giving a change in accordance with that reaction to the light in the hetero core formed at a surface side of said hetero core; and reflection means for reflecting light in the hetero core and returning the light to said optical fiber portion side at the surface of the end of the hetero core opposite to the end melt bonded to the optical fiber portion.

3. A measuring apparatus comprising:

an optical fiber sensor including an optical fiber portion for transmitting light;

mode restriction releasing means including a light permeable member melt bonded to a front end of the optical fiber portion, guiding at least a portion of the light transmitted by the optical fiber portion to the outside of a core to release a restriction of the mode of the light, and returning the light released in the restriction of the mode into the core, said mode restriction releasing means being a hetero core provided with a light transmitting core having a different diameter from the core of the optical fiber portion and able to transmit light propagated through the core and shorter in comparison with the length of the optical fiber portion; and further comprising:

a metal film provided at a surface side of said hetero core and generating surface plasmon by reflection of light in the hetero core at that surface; and reflection means for reflecting light in the hetero core and returning the light to said optical fiber portion side at the surface of the end of the hetero core opposite to the end melt bonded to the optical fiber portion;

a light source connected to an optical fiber portion side end of the optical fiber sensor and emitting light to the core of the optical fiber sensor; and a light detecting means for detecting direct intensity of returned light returning to the light source side via the core subjected to interaction with the outside of the mode restriction releasing means in the mode restriction releasing means.

4. The measuring apparatus as set forth in claim 3, further comprising:

measuring means for measuring a predetermined characteristic of an environment outside of said optical fiber sensor based on an intensity of said returned light detected by said light detecting means.

5. A measuring apparatus comprising:

an optical fiber sensor including an optical fiber portion for transmitting light;

mode restriction releasing means including a light permeable member melt bonded to a front end of the optical fiber portion, guiding at least a portion of the light transmitted by the optical fiber portion to the outside of a core to release a restriction of the mode of the light, and returning the light released in the restriction of the mode into the core, said mode restriction releasing means being a hetero core provided with a light transmitting core having a different diameter from the core of the optical fiber portion and able to transmit light propagated through the core and shorter in comparison with the length of the optical fiber portion; and a detection chemical immobilizing film selectively reacting with a detection object at the outside of said hetero core and giving a change in accordance with that reaction to the light in the hetero core formed at a surface side of said hetero core;

reflection means for reflecting light in the hetero core and returning the light to said optical fiber portion side at the surface of the end of the hetero core opposite to the end melt bonded to the optical fiber portion;

a light source connected to an optical fiber portion side end of the optical fiber sensor and emitting light to the core of the optical fiber sensor; and a light detecting means for detecting direct intensity of returned light returning to the light source side via the core subjected to interaction with the outside of the mode restriction releasing means in the mode restriction releasing means.

6. A measuring apparatus as set forth in claim 5, further comprising measuring means for measuring a predetermined characteristic of an environment outside of said optical fiber sensor based on an intensity of said returned light detected by said light detecting means.

* * * * *